US012303231B2

(12) United States Patent
McDaniel et al.

(10) Patent No.: US 12,303,231 B2
(45) Date of Patent: May 20, 2025

(54) SYSTEMS AND METHODS INCLUDING A DEVICE FOR PERSONALIZED ACTIVITY MONITORING INVOLVING THE HANDS

(71) Applicants: Arizona Board of Regents on Behalf of Arizona State University, Tempe, AZ (US); Mozest Goldberg, Les Baux de Provence (FR)

(72) Inventors: Troy McDaniel, Gilbert, AZ (US); Sethuraman Panchanathan, Gilbert, AZ (US); Mozest Goldberg, Les Baux de Provence (FR)

(73) Assignees: Arizona Board of Regents on Behalf of Arizona State University, Tempe, AZ (US); Mozest Goldberg, Les Baux de Provence (FR)

( * ) Notice: Subject to any disclaimer, the term of this patent is extended or adjusted under 35 U.S.C. 154(b) by 394 days.

(21) Appl. No.: 17/759,011

(22) PCT Filed: Jan. 25, 2021

(86) PCT No.: PCT/US2021/014951
§ 371 (c)(1),
(2) Date: Jul. 18, 2022

(87) PCT Pub. No.: WO2021/151090
PCT Pub. Date: Jul. 29, 2021

(65) Prior Publication Data
US 2023/0034807 A1 Feb. 2, 2023

Related U.S. Application Data

(60) Provisional application No. 62/965,353, filed on Jan. 24, 2020.

(51) Int. Cl.
A61B 5/00 (2006.01)
A61B 5/11 (2006.01)
(Continued)

(52) U.S. Cl.
CPC ............ A61B 5/004 (2013.01); A61B 5/1114 (2013.01); A61B 5/681 (2013.01); G06T 7/20 (2013.01);
(Continued)

(58) Field of Classification Search
CPC ... A61B 5/0077; A61B 5/0205; A61B 5/1112; A61B 5/1114; A61B 5/1117;
(Continued)

(56) References Cited

U.S. PATENT DOCUMENTS

D427,918 S 7/2000 Nakai et al.
10,129,503 B1 11/2018 Kim et al.
(Continued)

FOREIGN PATENT DOCUMENTS

WO 2015131157 A1 9/2015
WO 2022011344 A1 1/2022

OTHER PUBLICATIONS

Maekawa, Takuya, et al. "Object-based activity recognition with heterogeneous sensors on wrist." Pervasive Computing: 8th International Conference, Pervasive 2010, Helsinki, Finland, May 17-20, 2010. Proceedings 8. Springer Berlin Heidelberg, 2010. ( Year: 2010).*

(Continued)

Primary Examiner — Chineyere Wills-Burns
Assistant Examiner — Emmanuel Silva-Avina
(74) Attorney, Agent, or Firm — Polsinelli PC

(57) ABSTRACT

A computer-implemented system and associated methods are disclosed including a device for personalized activity monitoring using the hands. The device is worn about a wrist and captures images along the wrist including movement of the hands to monitor predetermined hand movements relative to an object of interest.

17 Claims, 17 Drawing Sheets

(51) Int. Cl.
G06T 7/20 (2017.01)
G06T 7/73 (2017.01)
G06V 20/00 (2022.01)

(52) U.S. Cl.
CPC .............. G06T 7/74 (2017.01); G06V 20/00 (2022.01); *G06T 2207/10016* (2013.01); *G06T 2207/20081* (2013.01); *G06T 2207/20084* (2013.01)

(58) Field of Classification Search
CPC ... A61B 5/1118; A61B 5/1122; A61B 5/1128; A61B 5/1125; A61B 5/681; A61B 5/6824; A61B 5/7267; G06F 18/22; G06F 18/24133; G06T 2207/10016; G06T 2207/20081; G06T 2207/20084; G06T 7/20; G06T 7/246; G06T 7/74; G06V 20/00
USPC ........................................................ 382/103
See application file for complete search history.

(56) References Cited

U.S. PATENT DOCUMENTS

| | | | | |
|---|---|---|---|---|
| 2004/0218474 | A1* | 11/2004 | Yamazaki | G04B 47/00 368/82 |
| 2008/0274819 | A1* | 11/2008 | Caldwell | A63B 69/3608 473/213 |
| 2011/0182469 | A1* | 7/2011 | Ji | G06V 40/20 382/103 |
| 2016/0034764 | A1* | 2/2016 | Connor | G06V 20/52 348/158 |
| 2020/0005615 | A1* | 1/2020 | Madden | G06F 18/22 |
| 2023/0335253 | A1* | 10/2023 | Connor | G06F 3/013 |

OTHER PUBLICATIONS

Alfeo, Antonio L., Mario GCA Cimino, and Gigliola Vaglini. "Measuring physical activity of older adults via smartwatch and stigmergic receptive fields." arXiv preprint arXiv:1901.00552 (2019). (Year: 2019).*

K. Kahol, P. Tripathi, S. Panchanathan, M. Goldberg. "Formalizing Cognitive and Motor Strategy of Haptic Exploratory Movements of Individuals who are Blind", The 3rd IEEE International Workshop on Haptic, Audio and Visual Environments and Their Applications, pp. 25-30, Ottawa, Canada, Oct. 2-3, 2004.

Riley Booth and Peter Goldsmith, "Detecting finger gestures with a wrist worn piezoelectric sensor array" 2017 IEEE International Conference on Systems, Man, and Cybernetics (SMC), Banff Center, Banff, Canada, Oct. 5-8, 2017.

Dementyev, Artem, and Joseph A. Paradiso. "WristFlex." Proceedings of the 27th Annual ACM Symposium on User Interface Software and Technology, UIST'14, Oct. 5-8, 2014, Honolulu, HI, USA. (2014). http://hdl.handle.net/1721.1/103642.

Rafael Rego Drumond, Bruno A. Dorta Marques2, Cristina Nader Vasconcelos2 and Esteban Clua2, "PEEK: An LSTM Recurrent Network for Motion Classification from Sparse Data", Proceedings of the 13th International Joint Conference on Computer Vision, Imaging and Computer Graphics Theory and Applications (VISIGRAPP 2018)—vol. 1: GRAPP, pp. 215-222.

Feng Zhao, Qingming Huang, and Wen Gao "Image Matching by Multiscale Oriented Corner Correlation", Asian Conference on Computer Vision , 2006, pp. 928-937.

Chen, H., Wang, Y., Wang, G., & Qiao, Y. "A low-shot transfer detector for object detection". Thirty-Second AAAI Conference on Artificial Intelligence, Apr. 2018.

Zou, Zhengxia & Shi, Zhenwei & Guo, Yuhong & Ye, Jieping. "Object Detection in 20 Years: A Survey", (2019. https://arxiv.org/pdf/1905.05055.pdf ).

Rezanejad, M., Downs, G., Wilder, J., Walther, D. B., Jepson, A., Dickinson, S., & Siddiqi, K. (2019). "Scene Categorization from Contours: Medial Axis Based Salience Measures", Proceedings of the IEEE Conference on Computer Vision and Pattern Recognition (pp. 4116-4124).

Redmon, J., & Farhadi, A. (2017). "YOLO9000: better, faster, stronger", Proceedings of the IEEE conference on computer vision and pattern recognition (pp. 7263-7271).

Kang, B., Liu, Z., Wang, X., Yu, F., Feng, J., & Darrell, T. (2018). "Few-shot Object Detection via Feature Reweighting", arXiv preprint arXiv:1812.01866.

Lancaster Wearable Watch Patent, 1886. http://www.historiccamera.com/cgi-bin/librarium2/pm.cgi?action=app_display&app=datasheet&app_id=1028.

https://www.zdnet.com/pictures/from-calculator-to-smartwatch-casios-featurecd-filled-ruggedized-trip-through-time/11/.

https://www.wired.com/2000/01/watch-look-and-listen/.

Greenwald, GoPro Digital HERO 3 Sports Wrist Camera.

Schilling T4 Write Camera Kit https://seatronics-group.com/equipment-rental/rov-tooling/manipulators-and-accessories/schilling-t4-wrist-camera-kit/.

Casio discounted: https://www.maxmax.com/aXRayCasioWristCamera.htm.

Yang et al., Crowd Activity Change Point Detection in Videos via Graph Stream Mining, 2018 IEEE/CVF Conference on Computer Vision and Pattern Recognition Workshops, 9 pages.

Kim et al., Digits: Freehand 3D Interactions Anywhere Using a Wrist-Worn Gloveless Sensor, 2012, 10 pages.

Maekawa et al., Object-Based Activity Recognition with Heterogeneous Sensors on Wrist, Conference Paper, May 2010, https://www.researchgate.net/publication/221015945, 19 pages.

https://www.apartmenttherapy.com/study-reveals-the-most-common-items-that-go-missing-at-home-246906. 2017.

* cited by examiner

SYSTEMS AND METHODS INCLUDING A DEVICE FOR PERSONALIZED ACTIVITY MONITORING INVOLVING THE HANDS

CROSS REFERENCE TO RELATED APPLICATIONS

The present document is a PCT patent application that claims benefit to U.S. Provisional Patent Application Ser. No. 62/965,353; filed on Jan. 24, 2020, which is herein incorporated by reference in its entirety.

TECHNICAL FIELD

The present disclosure generally relates to the fields of wearable computing, multimodal processing, and cognitive prosthetic devices; and more particularly, to a system including a device and methods for monitoring the hands to understand interactions and activities with and within an immediate environment.

BACKGROUND

In early infancy, through the hands, we learn to understand and "see" the world. Much of human activity requires and revolves around the use of the hands. When we use our hands, it is mostly at the subconscious level; hence, we do not explicitly reflect and control the movement of our hands. However, if we are able to monitor the hands and its immediate environment, then this provides insight into what we are planning, what tasks we are performing, and what tasks we have already performed.

It is with these observations in mind, among others, that various aspects of the present disclosure were conceived and developed.

SUMMARY

The present inventive concept relates to a device which monitors the hands and its immediate environment, and using algorithmic techniques for image and body sensor data analysis and activity recognition, identifies the specific action being undertaken. The idea for the present inventive concept comes from the confluence of many complementary fields including developmental psychology, neurology, cognitive neuroscience, image processing, neural networks, and deep learning. We use our hands to explore and interact with our surrounding environment, often at a subconscious level. Unobtrusively and discreetly capturing this information can provide a platform for monitoring, analyzing, recognizing, recalling, and predicting our interactions with the world around us.

Humans interact with the world around them through their hands. Therefore, monitoring the hands and its immediate environment can provide insight into what we are planning and the activities we are performing. Consider the following example: when we want to grasp an object, the brain prepares our hands and body from its understanding of the shape, texture, and weight of the object; our body turns towards the object and may change its stance, our hands move toward the object, and, at the same time, changes the shape of the hands to conform to the object. If at the same time, we can capture images of the object to be grasped, then we can use one of a number of image processing algorithms to identify the object being grasped. Once the object is grasped (held), it may be displaced and subsequently released from the hand; by detecting this release and the immediate environment where it was released, physical location of objects can be tracked. If the grasped object is used in some activity, then by monitoring the immediate environment and using one of a number of image processing algorithms, the task being performed can be identified; examples include (1) unlocking a door, (2) taking pills, (3) turning on the gas on a stove top, (4) feeding oneself, (5) executing a recipe, and (6) shopping or performing tasks from a list, to name a few. One important aspect of activity is memory and compliance. What have I done and have I performed this activity correctly: (1) Did I take the keys out of the door lock? (2) Which pills did I take? (3) Did I switch off the gas? (4) What and how much did I eat? (5) Did I carry out all the steps in the recipe? Further, (6) Did I buy all items or perform all tasks from my list? Although the examples provided concern daily personal activities, the same analysis holds true for a wide range of professional activities.

In view of the foregoing, in one embodiment, a device is disclosed which may be wrist-worn and measures the movement, position, and orientation of the wrist, hands and fingers, and simultaneously generates a video stream of the hand and fingers and their immediate environment. The resultant time-stamped data set includes multimedia/multimodal signal capturing motion (measured by acceleration using inertial sensors) information, activity of muscles and tendons below the skin (measured by displacement using pressure sensors), and images (captured by optical components). The device is not limited to these modalities; such that other sensors may be implemented to enhance the multimedia/multimodal signals extracted. For example, electromyography (EMG) can be employed to measure muscle response and electrical activity from the muscles to enhance the understanding of object interactions. In addition, ultrasonic sensors can be implemented to measure distance, or use infrared or thermal imaging in low light situations and even a Global Positioning System (GPS) chip for location.

In one embodiment, the device operates independently in the background, is unobtrusive, and does not interfere in any way with the movements of the hands and fingers. The possible placement of the device is on the wrist. One method of communication is voice for the user and a combination of visual and haptics for the device; however, the device can also be informed by communication through any computing device, whether handheld or fixed. In one embodiment, the device identifies or is fed with known locales; for example, a living quarter, an office, a car, or other defined environments. Objects within these locales are not lost but only misplaced. In unknown environments, for example, on a bus or in a store, objects are lost. A location is a particular fixed element within a locale, such as a drawer or a safe or could designate a piece of clothing or bag where individuals leave objects. A location can also be associated with respect to a place on the body; for example, a pocket in a piece of clothing, fingers with jewelry, and the mouth where food and drugs are ingested. In guided, user-centered initialization and machine-learning, the user informs the device of the objects, the locales, locations, and activities that he or she wishes to be monitored (i.e., the user defines a set of objects/locales/activities with which the device will be initialized). In a semi-autonomous mode, the system detects frequently occurring patterns of objects/locales/activities which are presented to the user for identification and subsequent monitoring by the device.

The device of the present disclosure can be used to track the location of a mobile object so as to inform the user of its final position when requested by the user. When a user reaches out for an object, the various multimodal signals can be captured. For example, the first indicates that the hand is in motion, the second that the fingers have changed position, and the third that the fingers have changed their configuration as the hand prepares itself to interact with an object.

One particular situation of interest is when an object is grasped by the hands and is displaced to some random position. At some point, the object will leave the grasp of the hand and the hand will retreat or move away. Because this subject motion takes a certain amount of time, there will be a set of frames from the video stream which will have views of the object and its surrounding environment from different distances and perspectives. The set of frames may be analyzed and the most suitable subset of frames showing the current location of the object is stored. When the user requests the location of the object, a set of pictures can be displayed to the user with sufficient detail to allow the object to be localized. In addition, the user may be informed when the object is left in a pre-defined locale. Special case: Tracking a predefined activity to verify compliance. A typical example would be: has an individual taken all his or her pills? Initialization involves first showing the pills that need to be taken, the motion towards the mouth and the release of the pill in the mouth. As the individual takes the pills, the devices tracks which pills are taken and ensures that they have been released into the mouth.

Possible usage scenarios are as follows: (1) Base activity of grasping and releasing an object; (2) Interacting with keys and other common objects, e.g., umbrella, passport, wallet, glasses, credit cards, and documents; (3) Turning off gas stove (safety); (4) Interacting with control panels; and (5) Taking pills (health). Complex activity monitoring including (1) Carrying out a recipe; (2) Exercise (3) Patient and elderly care; and (4) Playing a musical instrument.

Given the very wide range of applications areas, it is contemplated that the inventive concept is suitable for an embodiment in the form of a platform which allows developers to integrate and tailor the device to their particular needs by creating scripts. For example, elderly care and patient monitoring may require access to other sensors (for example, heart and glucose monitors), to communications channels and protocols of care.

One feature of the inventive concept is that it includes a method for monitoring the hands by positioning sensors at the wrist; in essence, providing a wrist-centric view of the activity. In one embodiment, two (or more) cameras are used: One video camera is placed on the dorsal side of the wrist to capture the immediate environment; and the second video camera is placed on the ventral side of the wrist to capture the fingers, hand, and object of interest. In addition, in one embodiment, the motion of the wrist is measured by acceleration using an inertial sensor, and the activity of muscles and tendons in the wrist are measured by displacement using pressure sensors. In its other instantiations, the present disclosure is not limited to two cameras; additional cameras may be added to reduce occlusion, and other sensors may be used. A second feature of the inventive concept is the use of the multimodal data set thus generated as input to a filter, which parses the data stream by looking for inflection points (changes) in the movement of the hands and fingers. The segments are then fed to an algorithm, which has been pre-trained to identify classes associated with basic actions, such as, moving forward, moving sideways or backwards, preparing the hand for touching, grasping, displacing, and releasing. The use of multimodal data sets allows the algorithm to efficiently hone in on significant actions, eliminating the need to process and store voluminous video data stream. Another feature is the initialization process, which yields a device customized to an individual's requirements. Yet another feature is that the device, making use of the video and GPS and other location sensors, can link the activity to pre-defined locales and locations.

Existing methods for monitoring activities of the hand generally require so-called smart environments where the space is equipped with cameras or the use of gloves with incorporated sensors to directly measure the movements of the hands and fingers. The former is expensive to set up and limited in geographic scope, whereas the latter places a burden on the hands and limits the activity that can be performed. Yet, the device of the present inventive concept is free to operate in a multitude of environments; for example, with the proper choice of image capture sensors, even in low light conditions. As the device is lightweight and placed on the wrist, it presents very little burden and does not interfere with the activity on hand; in certain cases, for example, when the clothing worn by the individual covers the device, modifications to the image capture could be made by, for example, making use of fiber optics to guide the light to the image sensor.

Furthermore, the solution encompassed by the present disclosure offers a very simple show and tell initialization process. The individual first selects from a list the objects, locales and activities he or she wishes to monitor and track, and for each, shows the device the object, the locale, and demonstrates the activity.

The inventive concept has the potential to dramatically reduce the time and nuisance of finding misplaced objects. The inventive concept also has the potential to significantly improve safety and health for the elderly, for patient care, and in many others areas where there is significant involvement of the hand and wrist.

The Inventive concept has significant potential to lead to a new class of products and associated services centered on monitoring human activity associated with the hand. Currently popular consumer products such as Fitbit and Apple's smartwatch focus on monitoring vital signs such as heart rate and acceleration. This allows them to measure normal activity such as walking/running and to report on potential problems such as irregular heart rate and falling. The inventive concept subsumes these functions and can monitor much more complex forms of human activity, all within the same physical device.

Current approaches to finding misplaced objects rely on relatively expensive hardware tags which added to the object of interest, are geographically limited, and are powered by batteries. One such popular device is Tile. The present inventive concept is not geographically limited, and requires no tags and associated batteries. The market for this class of device is very large.

Furthermore, there are currently no general purpose devices and platforms geared to monitoring a wide range of human activity. The present inventive concept can deal with a wide range of activity by exploiting knowledge of the specific activity and its context. There is very significant potential for commercializing a platform which offers developers the possibility to tailor the device for specific applications; examples include services for monitoring elderly, exercise compliance, food intake for diet control, and aids for individuals who are blind.

BRIEF DESCRIPTION OF THE DRAWINGS

Corresponding reference characters indicate corresponding elements among the view of the drawings. The headings used in the figures do not limit the scope of the claims.

DETAILED DESCRIPTION

As indicated herein, aspects of the present disclosure relate to a system including a device and associated methods for personalized activity monitoring using the hands. In one non-limiting embodiment, the device is adapted to be worn along the wrist similar to a wrist-watch or fitness band, and generally includes a dorsal camera, a ventral camera, a plurality of sensors, and a microcontroller that leverages multimodal data streams generated by the plurality of cameras and the plurality of sensors to monitor activity of the hand, and identify a predetermined activity or task of the hand relative to an object of interest.

Figure 1A:
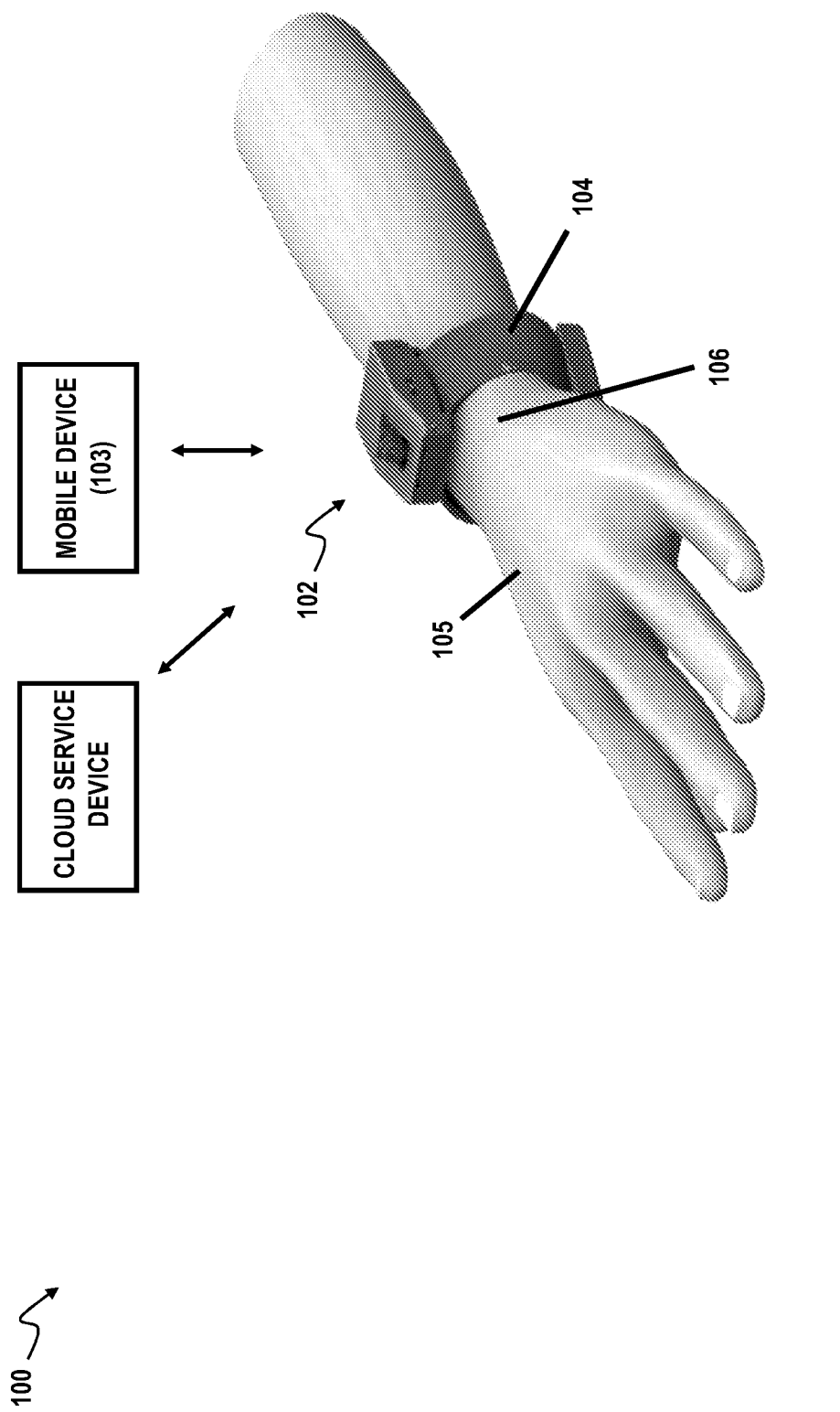
FIG. 1A is an isometric view of a graphical illustration depicting a system including a device worn along a wrist for personalized activity monitoring, according to one embodiment of the inventive concept described herein.
Figure 1B:
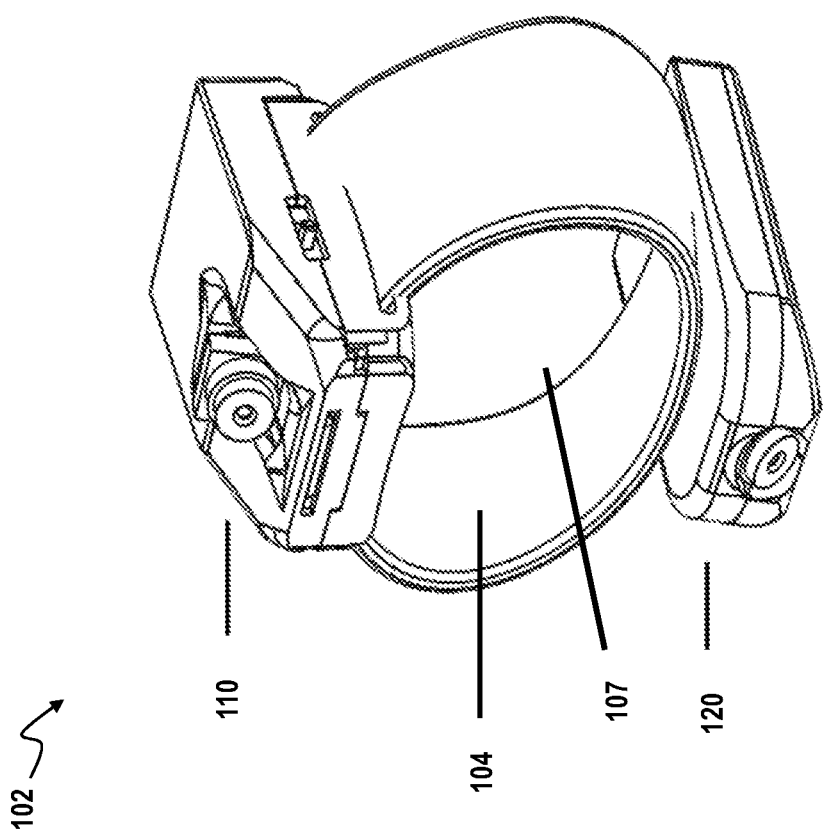
FIG. 1B is an isometric view of an illustration of the device of FIG. 1A.

Referring to FIG. 1A and FIG. 1B, a system 100 is shown including a device 102, which may be wrist-worn, and is otherwise advantageous for personalized activity monitoring using the hands. In general, the device 102 includes a band 104 in communication with two sensor main assemblies: a dorsal unit 110 coupled to a first portion of the band 104, and a ventral unit 120 coupled to a second portion of the band 104 opposite the dorsal unit 110. As indicated, the band 104 defines an opening 107 for receiving a human wrist 106 (of a human hand 105) so that a user can wear and operate the device 102 as described herein. During use, the ventral unit 120 rests along the bottom portion of the wrist 106, and the dorsal unit 110 is positioned over the top side of the wrist 106. Each of the dorsal unit 110 and the ventral unit 120 includes various electrical components for activity monitoring of the hands along different environments and perspectives, as described herein. The band 104 may be formed using any non-limiting materials and may include a general watch wrist-strap with hook and loop components for adjusting a size of the opening 107, an elastic band that can be temporarily expanded over the wrist 106 to adjust the opening 107, and the like. In addition, conductive wiring and/or electrical circuity (e.g., power cable 131 in FIG. 1C) may be integrated within or along the band 104 to electrically interconnect the dorsal unit 110 with the ventral unit 120.

Figure 1C:
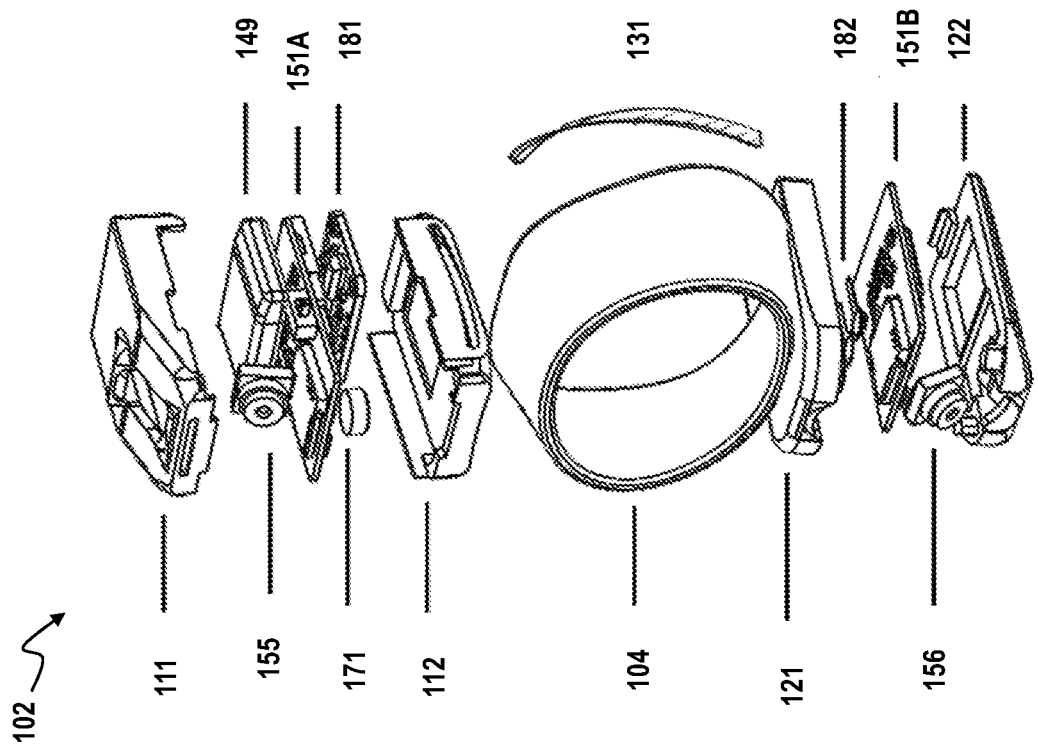
FIG. 1C is an exploded isometric view of an illustration of the device of FIG. 1A.

Referring to FIG. 1B and FIG. 1C, non-limiting hardware components such as various sensory modules of the device 102 are illustrated, including a dorsal camera 155 defined by the dorsal unit 110, and a ventral camera 156 defined by the ventral unit 120. In some embodiments, the dorsal camera 155, when the device 102 is worn along the wrist 106, is located on the dorsal side of the wrist 106 to collect video data of the surrounding environment. In one instantiation, the dorsal camera 155 includes a wide angle (100 degrees) camera device pointed towards the hand 105 and oriented at an 80 degree angle from the wrist 106. In other embodiments, the dorsal camera 155 includes multiple camera devices at different orientations. In some embodiments, when the device 102 is worn along the wrist 106, the ventral camera 156 of the ventral unit 120 is located along the ventral side of the wrist 106 to collect video data of any object to be identified relative to the wrist 106. In one embodiment, the field of view of the ventral camera 156 is 67 degrees, angled at 60 degrees from the wrist 106 pointed toward the hand 105. In other embodiments, multiple cameras may be employed, as well as auxiliary lights (visible or infrared) and night vision cameras.

As shown, the dorsal unit 110 includes a first housing portion 111, and a second housing portion 112 that mechanically connect to at least partially enclose the dorsal camera 155, and the second housing portion 112 of the dorsal unit 110 is coupled to the band 104. Similarly, the ventral unit 120 includes a first housing portion 121 and a second housing portion 122 that mechanically connect to at least partially enclose the ventral camera 156, and the first housing portion 121 of the ventral unit 120 is coupled to the band 104. The first housing portion 111 and the second housing portion 112 of the dorsal unit 110 and the first housing portion 121 and the second housing portion 122 of the ventral unit 120 at least partially enclose, secure, and protect the various sensors and electrical components of the device 102 further described herein.

Figure 1D:
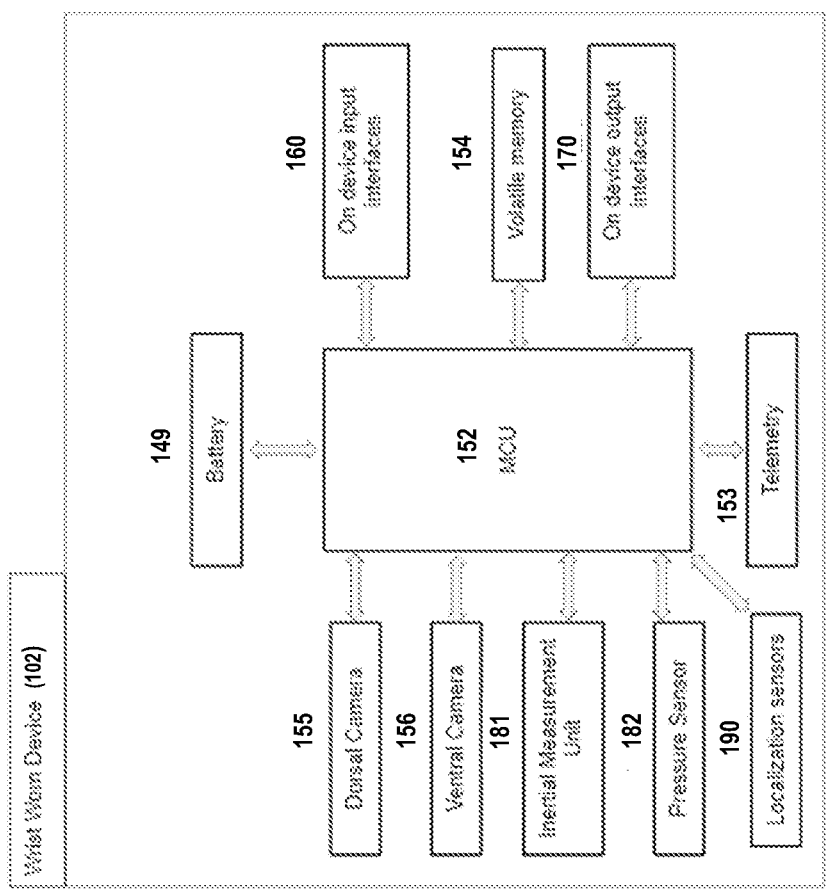
FIG. 1D is a simplified illustration of a high-level overview of hardware architecture associated with the device of FIG. 1A.
Figure 2A:
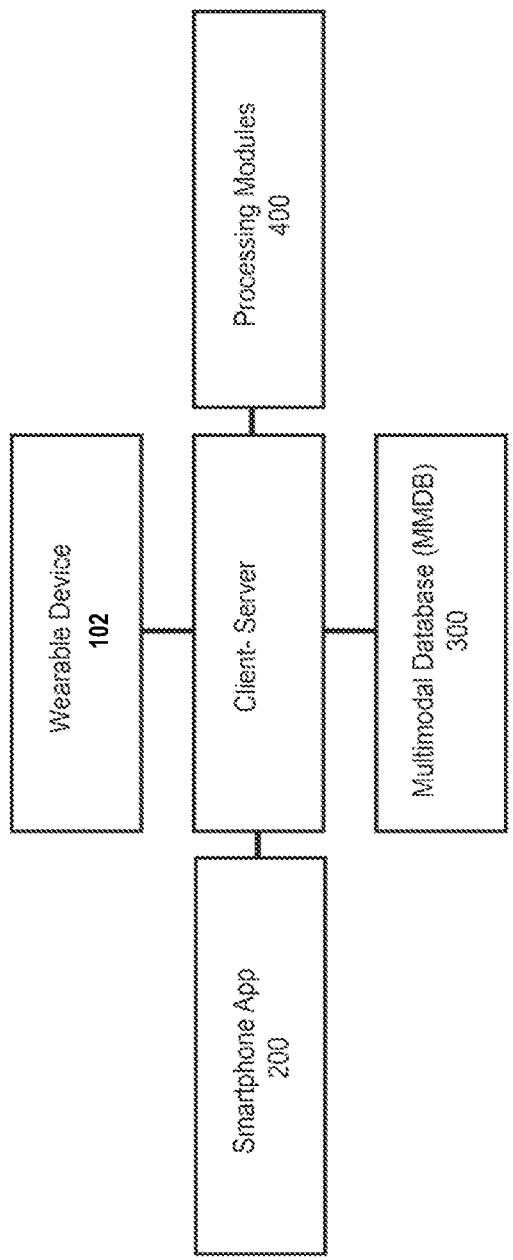
FIG. 2A is a simplified illustration of a possible server-client architecture which may be implemented along with the device of FIG. 1A.

As further shown, the device 102 includes one or more of a printed circuit board (PCB) 151, shown as PCB 151A and PCB 151B, and one or more of a microcontroller 152 (shown in FIG. 1D) or processing element/processor positioned along one or more of the PCB 151A or the PCB 151B, which connects the various sensory modules, including the dorsal camera 155, the ventral camera 156, hand/wrist sensors 181 and hand/wrist sensors 182, and location sensors 190. The microcontroller 152 handles on-device user interactions through onboard input interfaces 160 and output interfaces 170. The microcontroller 152 further communicates with a mobile application, also referred to herein as an "App" (200 in FIG. 2A) executable by the mobile device 103 (which may include a mobile phone or other mobile device) by way of a telemetry unit 153 (FIG. 1D).

In general, the mobile device 103, executing the mobile application 200, provides a visual display, a voice query interface, and supplementary localization interfaces. Some supplementary localization interfaces on the mobile device may include: Bluetooth, Near Field Communication (NFC), WiFi, and Global Positioning System (GPS).

Inertial Measurement Unit (IMU) of the Hand/Wrist Sensors (181)

The hand/wrist sensors 181 of the device 102 shown may include one or more of an IMU such that device 102 may utilize auxiliary means to sense the state of the wrist 106 to augment video collection for the purposes that would include, but are not limited to, improved battery life and object classification. In some embodiments, an inertial measurement unit (IMU) is used to collect linear acceleration along the X, Y, and Z axes; angular velocity along the X, Y, and Z axes; and the magnetic field strength along the X, Y, and Z axes. The device 102 also implements algorithms to fuse the data streams from any IMU of the hand/wrist sensors 181 to produce the absolute orientation of the device 102. Data from all of the sensors of the device 102 and the fused stream may be collected at 20 Hz. In other embodiments, different inertial sensors may be used.

Pressure Sensor of the Hand/wrist Sensors (182)

In some embodiments, the hand/wrist sensors 182 include at least one pressure sensor. For example, the hand/wrist sensors 182 may include a linear array of three resistive pressure sensors positioned on the ventral side of the wrist 106 on a line perpendicular to the fingers of the hand 105. In particular, the pressure sensors may be pressed against the forearm approximately 4 centimeters proximal from the wrist 106. In some embodiments, the pressure sensors are approximately 3 millimeters in diameter and are spaced 4 millimeters from center to center, and are used to capture movements in the fingers of the hand 105 and collect data at 100 Hz. In other embodiments, other types of pressure sensors placed in different configurations may be used.

Microcontroller (152)

The microcontroller 152 may include any processing element adapted to process data streams generated from the sensor modules (dorsal camera 155, the ventral camera 156, hand/wrist sensors 181 and hand/wrist sensors 182, and location sensors 190) to extract and utilize relevant information. The hardware to complete various aspects of the data processing pipeline can be fluidly shared between local processing on the device 102, on a connected mobile phone (e.g., mobile device 103) or even remotely on a cloud service. In one embodiment, data is streamed from the device 102 to a remote service for data processing.

Telemetry (153)

In some embodiments, the device 102 is adapted to communicate with external systems wirelessly for purposes that would include, but are not limited to, additional data processing and visual user interfaces. In one embodiment, the data is sent wirelessly using 2.4 GHz WiFi. However, the device 102 may be equipped with any number of antennae devices or electrical components to communicate through, e.g., Bluetooth, cellular communication channels, and the like.

Battery (149)

The device 102 includes at least one of a battery 149 to power the various electrical components included and described herein. In one embodiment, the battery 149 includes a 300 mAh lithium ion battery.

On-Device Input Interfaces 160

As indicated in FIG. 1D, the device 102 includes one or more on-device input interfaces 160 or any means by which to query it through a voice interface utilizing an onboard microphone. The device 102 may also include a means by which it can be manually configured in any form using buttons, switches, or lens covers for the purposes of turning off any camera, or other sensors during private situations such as using the bathroom, meetings, and so forth.

On-Device Output Interfaces (170)

As further indicated in FIG. 1D, the device 102 may further include any number of on-device output interfaces 170 or any means by which to notify the user. These could include, but are not limited to, haptic motors (171), LED lights, and display screens.

Localization Sensors (190)

The device 102 may also include additional means by which to localize itself in the environment. Accordingly, as further shown in FIG. 1D, the device 102 may include localization sensors 190 such as, but not limited to, GPS, Bluetooth, NFC, Radio-Frequency Identification (RFID), Ultra High Frequency RFID.

Volatile Memory (154)

The device 102 may also include a volatile memory (154) unit to act as a buffer for captured images before they are sent to external devices such as the mobile device 103. As depicted in FIG. 1C and FIG. 1D, the hardware components of the device 102 may include two main functional assemblies: the dorsal Unit 110 and the Ventral Unit 120. Both units are affixed to the band 104 defining a wrist cuff, and are electrically connected. In one embodiment, both units house an MCU (152) and Telemetry 153 on a respective printed circuit board (PCB) (PCB 151A and PCB 151B). The dorsal Unit 110 also contains the Dorsal Camera 155 and a Battery 149. The Ventral Unit 120 houses the ventral camera 156. In one embodiment, the Ventral Unit 120 further houses an array of pressure sensors (182).

Software Components

In one embodiment, a server-client architecture (FIG. 2A) is employed to coordinate communication between the device 102, the App 200 running on a smartphone or other such mobile device 103, a multimodal database (300) (MMDB), and any number of processing modules (400). The processing modules may include on-board processing elements of the device 102, remote processing elements such as one or more processors of a cloud or remote devices, or combinations thereof.

Figure 2B:
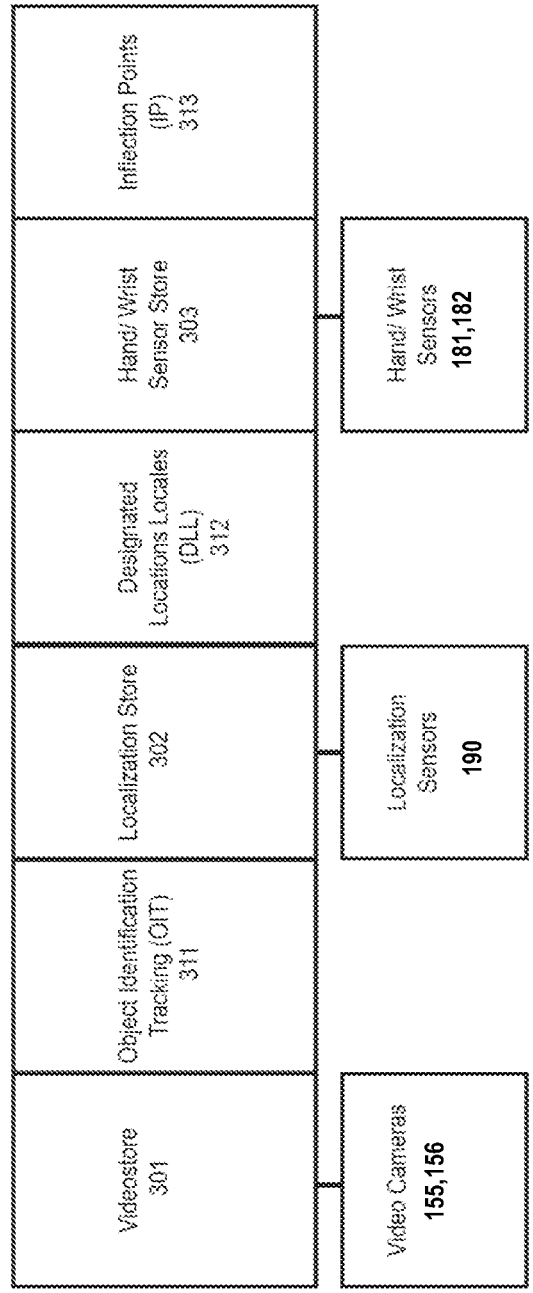
FIG. 2B is a simplified illustration of a multimodal database which may be implemented along with the device of FIG. 1A.

Multimodal Database (MMDB) (FIG. 2B):

In one embodiment of the present disclosure, a multimodal database 300 is implemented by the system 100 to store both the original and processed sensor data (FIG. 2B) of the multimodal data acquired by the device 102. In one implementation, there are three types of sensory data and distinct stores of the multimodal data: video input (from the camera 155, and the camera 156) as video storage (301), localization sensors (190) as storage (302), and hand/wrist sensors (181, 182) as storage (303). Three types of the processed multimodal data are distinguished: object identification and tracking (01T) (311), designated locations and locales (DLL) (312), and inflection points (IP) (313). Two initialization set-up steps may be employed when an individual first starts to use the device 102 and when new objects, locales and locations are added.

Figure 2C:
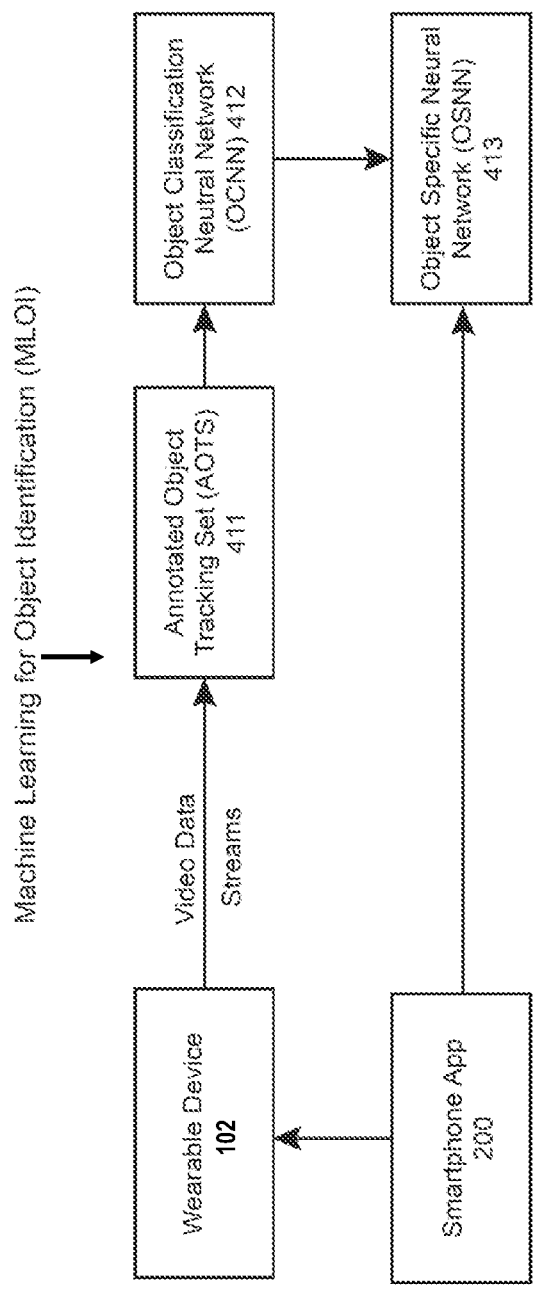
FIG. 2C is a simplified illustration of machine learning for object identification (MLOI) which may be implemented along with the device of FIG. 1A.

Machine Learning for Object Identification (MLOI) (FIG. 2C):

In one embodiment, machine learning involves starting with a small set of commonly misplaced or lost objects; the statistics of which are reported in the following study, to which the user can add other objects. Any number of convolutional neural network techniques may be employed for object detection and identification.

More specifically, for example, a convolutional neural network (OCNN) (412) may be leveraged, which has been trained to perform object detection. While wearing the device (102), for each object of interest, a user may be instructed through the App 200 on the smartphone to grasp, displace and release the object a number of times, effectively creating an Annotated Object Training Set (AOTS) (411).

Next, the OCNN model may be extended to detect objects of interest gathered using (AOTS) (411) employing any number of transfer learning techniques. In one embodiment, to decrease the burden on the user, (AOTS) (411) may be relatively small so necessitating the use of low shot transfer learning methods. The resultant Object Specific Neural Network (OSNN) (413) may then be used to identify the specific objects of interest to the user.

Figure 2D:
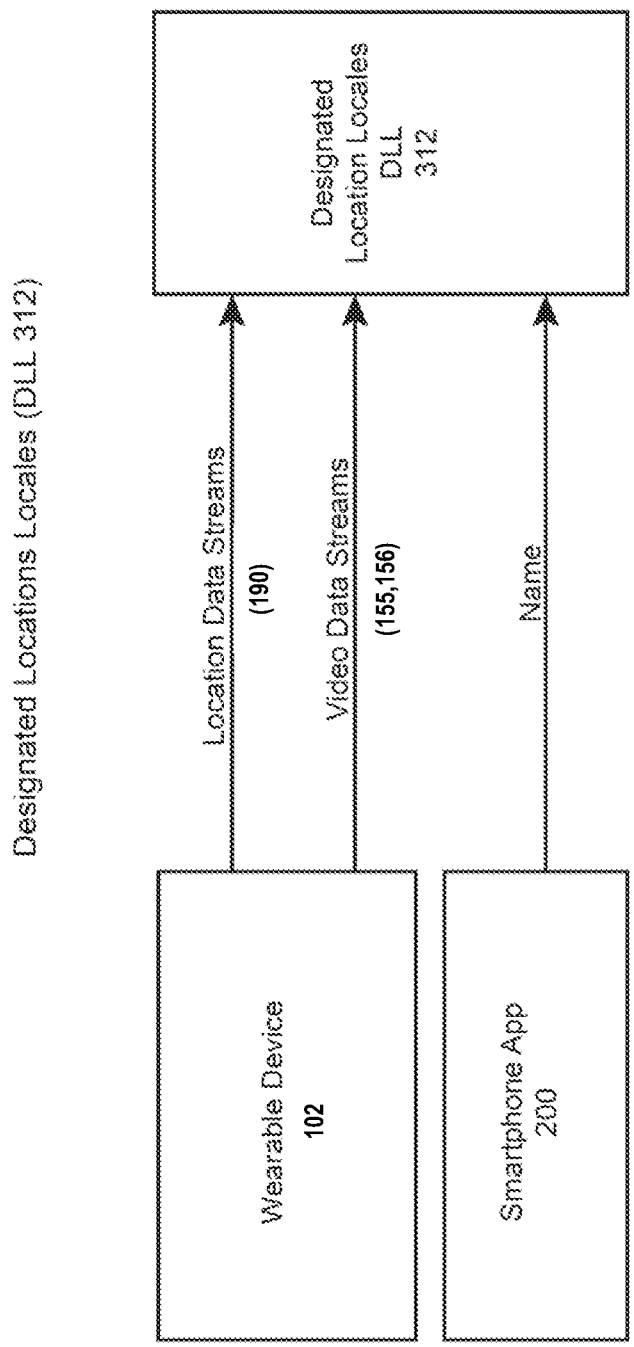
FIG. 2D is a simplified illustration of designated locations and locales (DLL) which may be implemented along with the device of FIG. 1A.

Designated Locations and Locales (DLL) Database 312 (FIG. 2D):

The purpose of this module and database is to allow the user to designate locations and locales. In one embodiment, while wearing the device 102, for each locations and locales, the user is instructed through the App 200 to carry out a set of actions. For example:

Step 1: The user associates a name with the DLL 312 through the App 200 and the mobile device 103 or otherwise.

Step 2: For a designated location: the user is requested to first point to the designated location, then approach it, and move away from it. For a locale: the user is requested to sweep the locale with several movements of the wrist, effectively capturing panoramic views of the locale. During these movements, the data streams from the video cameras (155,156) and from the location sensors (190) are acquired and entered into the (DLL) database (312). The video data undergoes image-edge based processing to create a series of edge images; in one embodiment one from the many well-known feature extractors has been implemented.

Figure 2E:
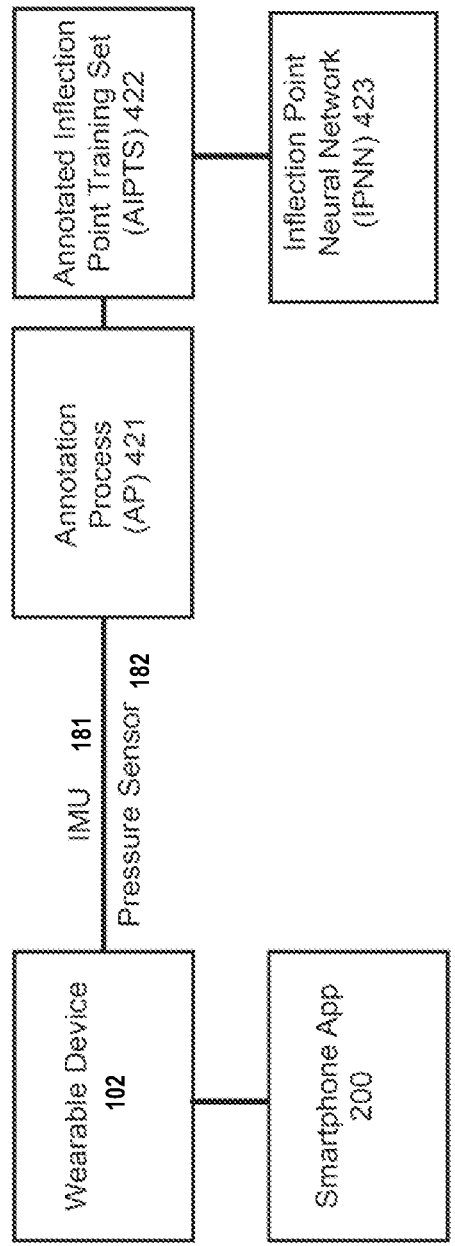
FIG. 2E is a simplified illustration of machine learning for inflection point extraction (MLIPE) which may be implemented along with the device of FIG. 1A.

Machine Learning for Inflection Point Extraction (FIG. 2E):

This module trains a Neural Network to identify and classify inflection points in the hand movements using the Hand-Wrist sensor data acquired by the device 102. In one embodiment the following inflection points are defined: the approach towards an object of interest, a change of direction in the approach, the grasping of the object, the displacement of the object, the release of the object and the retreat or movement away from the released object.

While wearing the device 102, for each object of interest, each user is instructed through an application (App) 200 on the smartphone (mobile device 103) to reach for, grasp, displace and release the object a number of times. The associated Wrist-Hand sensor data is annotated (subjected to an annotation process 421) and entered into the Annotated Inflection Point Training Set (AIPTS) 422. The AIPTS 422 is then used to train the Inflection Point Neural Network (IPNN) 423.

Designated Location Processor (DLP) (FIG. 2F):

This module is activated when an object has been grasped and released. It serves to situate the individual user and object in a designated locale and, if need be, further pinpoints the object to a designated location.

The module receives inputs from the specialized localization sensors 190 and interrogates the DLL 312 to determine whether the individual user or object is located within a known locale. If the sensor data from the localization sensors 190 is not of sufficient precision to determine the location, then the DLP uses the video data (from cameras 155,156) from the device 102 and compares these with those stored in the DLL 312. In one embodiment the Video Image Matcher (VIM) 431 implements a method for matching two images by spatial cross-correlation using either edge information or corner-like features found within the two images. The best matched location is then stored in the OIT 311.

Figure 2F:
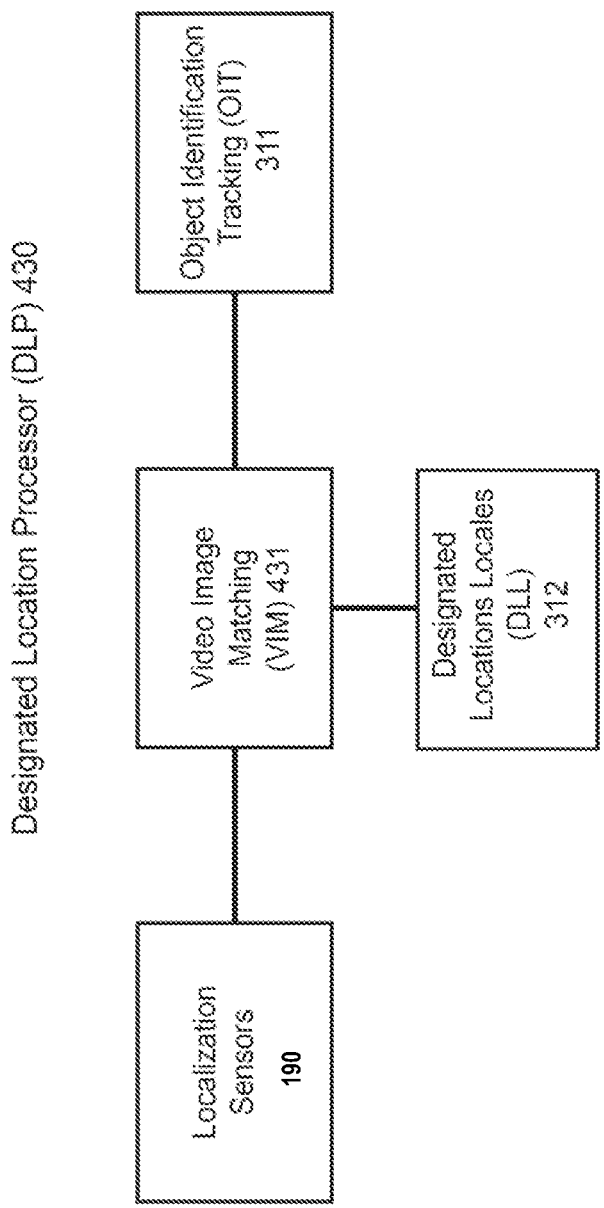
FIG. 2F is a simplified illustration of a designated location processor (DLL) which may be implemented along with the device of FIG. 1A.

Object Identification and Tracking (OIT) (FIG. 2G):

This module instantiates the two neural network classifiers, the IPNN 423 and the OSNN 413 and the DLP 430 (FIG. 2F). In its one embodiment, IPNN 423 operates continuously in the background whenever the device 102 is operational. It classifies the Wrist/Hand sensor data from the sensors 181,182 and stores the resultant time-stamped inflection points 313. For a special case when an object is grasped and then released, a time-stamped Grasping-Release Cycle can be defined (which extends in time on both sides to include the approach to the object and the retreat from the object).

When a grasping action is noted, the IPNN 423 groups and stores all the classified Inflection Point data 313 within the Grasping-Release Cycle. It also informs the OSNN 413, and the latter fetches from the inflection points 313 associated with this grasping action. The time-stamps on the inflection points 313 are used to determine which frames from the ventral camera data 156 to retrieve from the Video Store 301.

In one embodiment, the OSNN 413 attempts to identify the object being grasped frame-by-frame, starting with the frame (image) when the object is grasped and working backwards (in time) on the frames along the approach path. If a known object of interest is identified, the OIT database 311 is updated and the video data (from cameras 155, 156) and Inflection Points 313 for the entire Grasping-Release Cycle are retained. If no known object of interest then the data can be discarded.

Object Spatial Contextual Recall (OSCR) (FIG. 2H):

This module answers the user query, "Where is my object". In one embodiment the user inputs the request by voice through the App 200 executed on a mobile device 103 such as a smartphone using an on-board microphone (FIG. 2H). This request is translated into text using the on-board voice-recognition software. The request is transmitted to the Spatial Contextual Engine (SCE) 432 which retrieves the locale/location from the OIT Database 311 and this is reported on the display 201 of the mobile device 103, which may be touch-sensitive. If requested by the user, this can be followed up with video/image data from the DLL 312.

In parallel, the SCE 432 retrieves from the Inflection Points 313 of the last Grasping-Release Cycle for the requested object. The Inflection Point corresponding to the release of the object is then used to locate from the video store 301 the video frames captured by the dorsal camera 155 just before and after the object has been released. The retrieved video is sent to the display 201, where the user can then scroll through the video in both directions, freeze on a frame at any time, and zoom in and out; all under finger control, or via haptics.

Activity Monitoring by Scripting:

The purpose of this facility is to allow the user to create scripts for storage in memory of the device 102 and executable by the microcontroller 152, which instruct the device 102 to monitor user behavior and intervene when necessary. The potential of scripting will be illustrated by three examples.

Example #1 (FIG. 3A): One possible script that can be generated and implemented by the microcontroller 152 or otherwise accommodates retrieval of a credit card after paying. The credit card can be defined a designated object using the Machine Learning for Object Identification module, the billfold or wallet as a designated location using the Designated Locations and Locales database 312, and a flag can be set in the Object Identification and Tracking (OIT) database 311 to inform the subject "Credit Card Script" when the card is grasped. When the credit card is released, the Credit Card Script queries the Designated Location Processor 312 to confirm that it is not in a designated locale. When the user releases the credit card, the IMU data is continuously monitored and a warning is sent to the user if the distance to the last position of the card exceeds a threshold value. If the card is returned to the designated location then the Credit Card Script is deactivated.

Example #2 (FIG. 3B): Suppose we take out a designated object from a safe, which has previously been defined as a designated location. The device 102 can be programmed or otherwise configured to inform if the object has not been returned to the safe by a certain time, T. The subject "Safe Script" will need to add a flag in the Object Identification and Tracking 311 database such that, when the designated objected is grasped and displaced to a new location, the script is informed. If the object is returned to the safe before time T, the Script is informed and deactivated. If at time T the designated object has not been returned to the safe, the user can be informed by way of the app 200 executed by the mobile device 103.

Example #3 (FIG. 3C): A "Pill Script" executable by the microcontroller 152 addresses the common everyday problem of forgetfulness. Did I take my pill this morning? If not, remind me. We define the pill as a designated object, the mouth as a designated location, and set a flag to inform the Pill Script when the pill is grasped. If the pill is released into the mouth then the Script is informed. When the user asks the question, then the Script is in a position to answer; the pill has been released into the mouth, the pill has not been grasped, the pill has been grasped and moved. In the latter case the Pill Script invokes the Object Spatial Contextual Recall (432) module with the search item set to pill and shows the position of the pill to the user on the display 201.

Concatenating these basic operations and introducing more complex condition testing can create more complex scripts. For example, by repeating the steps from Example 3 above, a script can be generated and implemented to check whether an individual has taken all of his prescribed pills at a single session. In an analogous manner defining the briefcase as a designated location could accommodate generation of a script to check whether an individual places a set of designated objects in a briefcase before leaving for work. In a professional environment such as a hospital the device could monitor whether a nurse has administered a specific drug to a patient.

The software components of the server-client architecture described herein may include any number of components or modules executed by the microcontroller 152 or otherwise implemented, and may be implemented as code and/or machine-executable instructions executable by the microcontroller 152 that may represent one or more of a procedure, a function, a subprogram, a program, a routine, a subroutine, a module, an object, a software package, a class, or any combination of instructions, data structures, or program statements, and the like. In other words, one or more of the software components described herein may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a computer-readable or machine-readable medium, and the microcontroller 152 or other processing element (e.g., processor of the mobile device 103) performs the tasks defined by the code.

Figure 4:
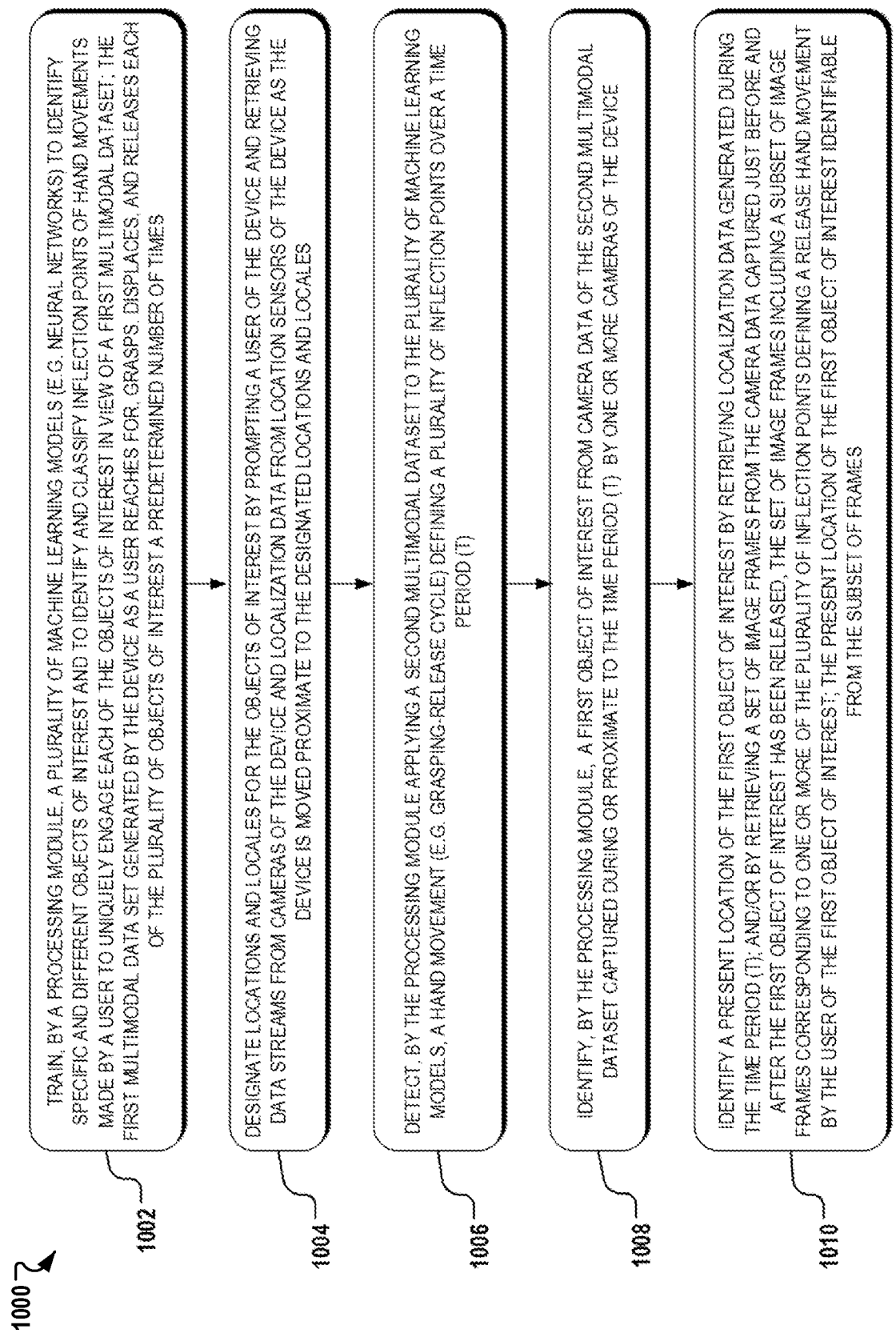
FIG. 4 is a flowchart illustrating a possible method associated with the system of FIG. 1A for personalized activity monitoring using the hands.

Referring to FIG. 4, a method or process 1000 associated with the system 100 and the device 102 is illustrated. Aspects of the process 1000, including computational functions and machine learning, may be performed by one or more of the processing modules 400, on-board processing elements of the device 102, remote processing elements such as one or more processors of a cloud or remote devices, or combinations thereof. It should be appreciated that the process 1000 is exemplary and non-limiting, such that additional steps, features, and sub-features are contemplated as described herein.

As generally indicated in block 1002 of process 1000, the device 102 may be subjected to a training and/or initialization phase with or without assistance by a user such that the device 102 is adapted for object identification, localization, and inflection point extraction. A plurality of machine learning models/algorithms is trained and tuned in view of a first multimodal dataset generated and stored in the MMDB 300 as the device 102 is implemented during this phase. The first multimodal dataset includes video/camera data captured by the camera 155 and the camera 156, data generated by the localization sensors 190, and data generated by the hand/wrist sensors 181,182 as the user engages with one or more objects of interest, and/or as the device 102 is implemented to capture some training/initialization information about each object of interest. For example, to generate the first multimodal dataset, the device 102 may be positioned proximate to or oriented towards each of a plurality of objects of interest, and/or while the user dons the device 102, the user reaches for, grasps, displaces, and releases each object a predetermined number of times.

In one example, a first neural network (OSNN 413) for detecting objects of interest may be generated, trained and tuned according to predetermined/desired parameters and objectives. The OSNN 413 maybe generated and configured to detect and distinguish the objects of interest by feeding a general convolutional neural network 412 with the Annotated Object Training Set (AOTS) 411 as described herein; which may be created from the first multimodal dataset, or otherwise created.

Similarly, a second neural network, the Inflection Point Neural Network (IPNN) 423, may be generated and trained to identify and classify inflection points in the hand movements as the hands of the user engage each object of interest using the Hand-Wrist sensors (181,182) data acquired by the device 102 during generation of the first multimodal dataset. In some embodiments, the associated Wrist-Hand sensor data is annotated (subjected to an annotation process 421) and entered into the Annotated Inflection Point Training Set (AIPTS) 422. The AIPTS 422 is then used to train the IPNN 423. In one embodiment the following non-limiting inflection points are defined: the approach towards an object of interest, a change of direction in the approach, the grasping of the object, the displacement of the object, the release of the object and the retreat or movement away from the released object.

In some embodiments, the AIPTS 422 maps specific movements, positions, and orientations of one or more hands (including the wrist, fingers, etc.) of the user wearing the device 102 for each inflection point corresponding to each object of interest, as extrapolated from the first multimodal dataset. For example, the AIPTS 422 may inform that for a first inflection point, a grasp, associated with a first object of interest, a pill, the pointer finger and the thumb of the right hand of the user make contact with opposite ends of the pill to form the grasping inflection point, shown in the left portion of FIG. 3C. The AIPTS 422 may further inform about a transition to and/or presence of another inflection point, such as the inflection point shown in the right portion of FIG. 3C. As shown in this right portion of FIG. 3C, the pointer finger and the thumb maintain a similar position and orientation relative to the pill to maintain a grasping motion, but the orientation of the hand relative to the wrist has changed; the hand is twisted back towards the user so that the user can consume the pill. This particular position, and orientation of the hands, wrist, and fingers may be mapped to a consumption inflection point. Feeding the subject inflection point extraction information to the IPNN 423 as training data, the IPNN 423 learns to identify a subsequent grasping inflection point and consumption inflection point of the pill by the user from subsequent multimodal data or subsequent multimodal datasets generated by the device 102 and fed to the IPNN 423 as implemented by one or more of the processing modules 400.

In some embodiments, the AIPTS 422 further tracks inflection points over a period of time (t) for each object of interest. In other words, during training, the AIPTS 422 extracts at least three inflection points from the images shown in FIG. 3C: the grasping inflection point, the consumption grasping point, and a release inflection point (not shown) over a time period (T). Tracking when certain inflection points associated with an object of interest generally occur over a given historical time period can inform the IPNN 423 when certain inflection points are likely to occur, and/or when transitions from one inflection point to another are likely to occur.

Referring to block 1004 of process 1000, locations and locales can be designated for each object of interest, and the subject information can be stored in the DLL database 312 for reference by the one or more processing modules 400. In some embodiments, during training as the first multimodal dataset is generated, this information is learned or is received from a user communicating through the App 200 via the mobile device 103, or otherwise. To illustrate, referencing the example of FIG. 3C, the user may associate a name of the location of the box of pills/pill box shown in the left portion of FIG. 3C, thereby created a designated location for the pills. The user may then be requested to first point to the designated location and the box of pills, then approach it, and move away from it. The user may further be requested to sweep the locale with several movements of the wrist, effectively capturing panoramic views of the locale proximate to the box of pills. During these movements, the data streams from the video cameras 155,156 and from the location sensors 190 are acquired (first multimodal dataset) and entered into the (DLL) database 312. The video data undergoes image-edge based processing to create a series of edge images, and feature extractors may be implemented to identify visual characteristics associated with the designated location of the pill box and its surrounding environment. In this manner, the device 102 is configured to recognize the location of the pill box and learn that the location is the designated location for the pills.

Figure 2G:
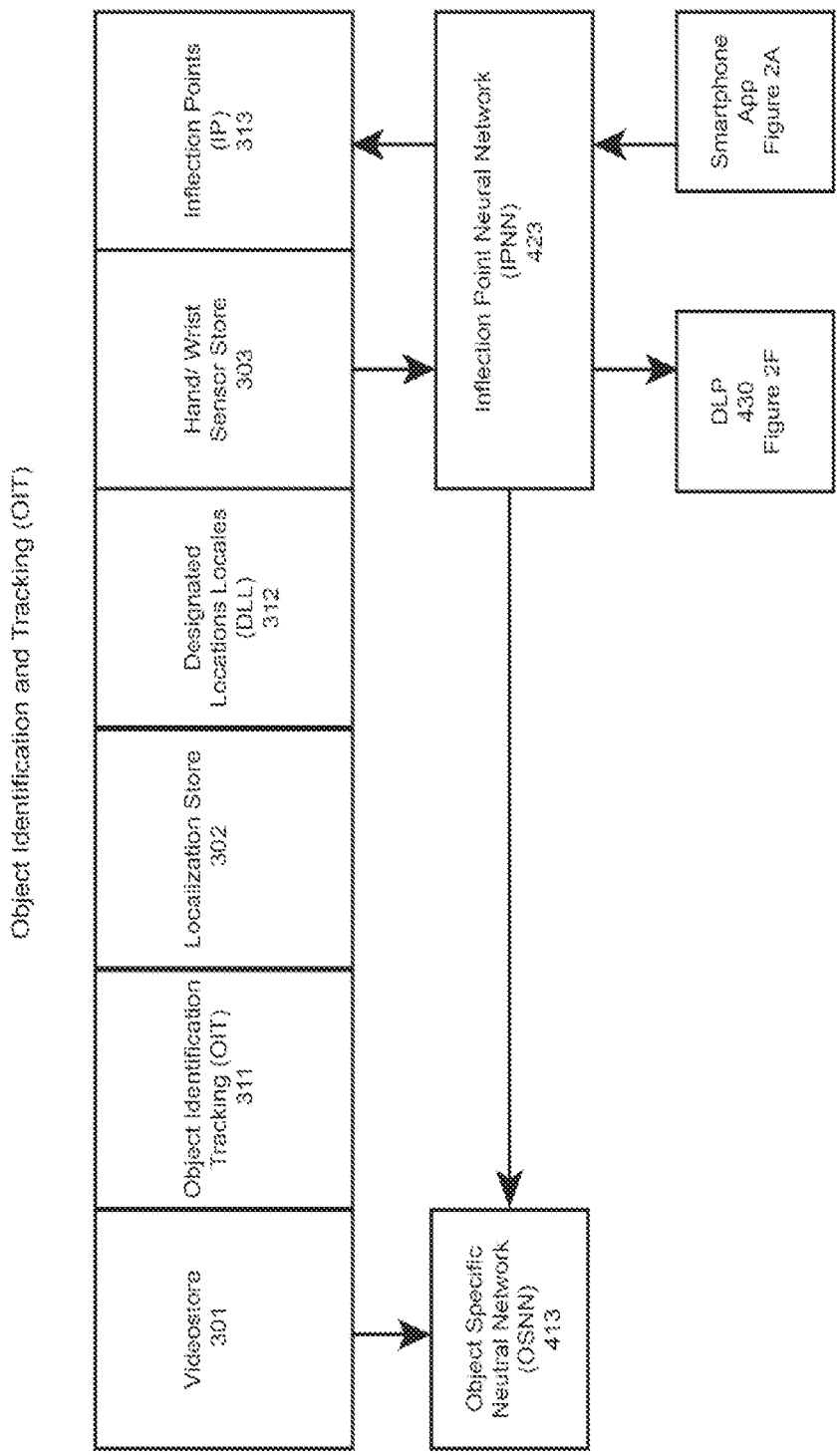
FIG. 2G is a simplified illustration of object identification and tracking (OIT) which may be implemented along with the device of FIG. 1A.
Figure 2H:
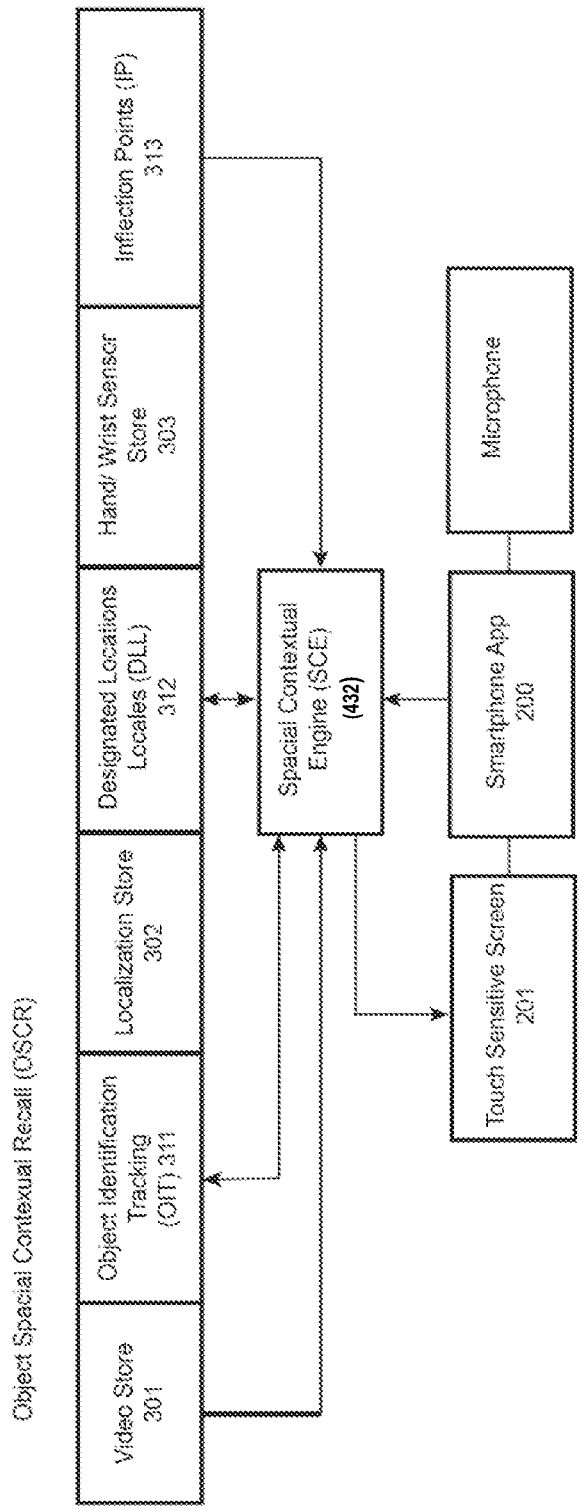
FIG. 2H is a simplified illustration of object spatial contextual recall (OSCR) which may be implemented along with the device of FIG. 1A.

Referencing blocks 1006 and 1008 and FIG. 2G, the device 102 and the trained plurality of machine learning models (e.g., the OSNN 413 and the IPNN 423), in view of the DLL database 312, allow the system 100 to be implemented for subsequent object detection, localization, and identification of inflection points informative as to some activity the user performs relative to an object of interest, or otherwise over a time period (T). Specifically for example, a second multimodal dataset (video/camera data captured by the camera 155 and the camera 156, data generated by the localization sensors 190, and data generated by the hand/wrist sensors 181,182) is generated as the user implements the device 102 for some predetermined amount of time. The IPNN 423 is executed using one or more of the processing modules 400 to identify a hand movement from the second multimodal dataset. Referring again to FIG. 3C, one example of the identified hand movement from the second multimodal dataset is a grasping and release engagement of the pill. The system 100 identifies the engagement of the pill as follows.

Once the second multimodal dataset is acquired, the IPNN 423 as implemented accommodates recognition of one or more inflection points associated with the pill object of interest, allows classification/identification of the Wrist/Hand sensor data of the second multimodal dataset generated from the sensors 181,182 and stores resultant time-stamped inflection points 313. A time-stamped Grasping-Release Cycle can be defined as the pill of FIG. 3C is grasped and then released, which extends in time on both sides to include the approach to the pill and the retreat from the pill, as the pill is released into the mouth of the user (not shown).

For example, when a grasping action of the pill is identified by the IPNN 423 in view of the second multimodal dataset, the IPNN 423 groups and stores all the classified Inflection Point data 313 within the Grasping-Release Cycle. It also informs the OSNN 413, and the latter fetches from the inflection points 313 associated with this grasping action. The time-stamps on the inflection points 313 are used to determine which frames from the ventral camera data 156 to retrieve from the Video Store 301 to show the user's engagement with the pill.

The OSNN 413 may be implemented to attempt to identify or confirm that the pill is in fact the object being grasped by referencing camera data of the second multimodal dataset captured during or proximate to the time period (T). In one embodiment, the OSNN 413 is implemented to scan the subject camera data, frame-by-frame, starting with the frame (image) when the object is grasped and working backwards (in time) on the frames along the approach path. If the pill is identified or confirmed as the object of interest, the OIT database 311 is updated and the video data (from cameras 155, 156) and Inflection Points 313 for the entire Grasping-Release Cycle are retained. If no known object of interest then the data can be discarded.

Figure 3A:
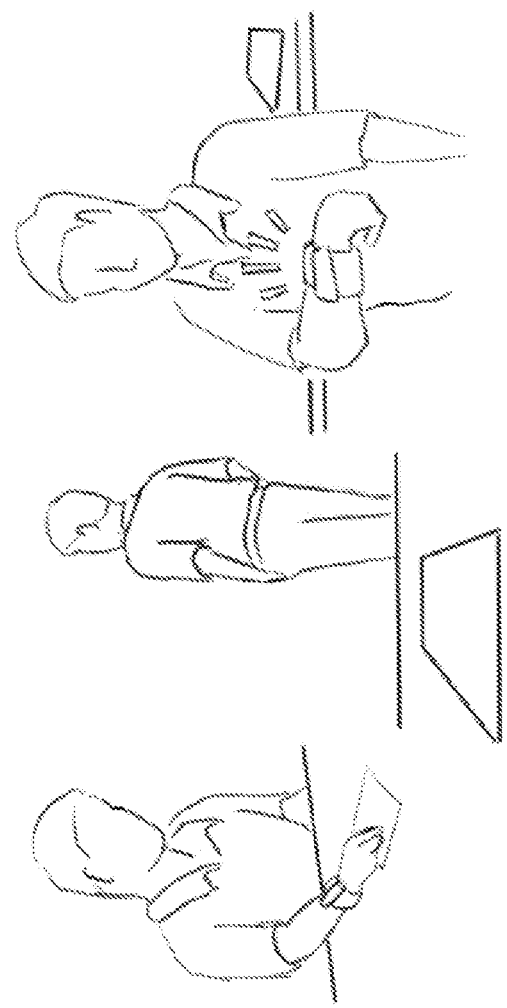
FIG. 3A is an illustration demonstrating one application of the device of the present disclosure for retrieving a credit card where the location has been forgotten.
Figure 3B:
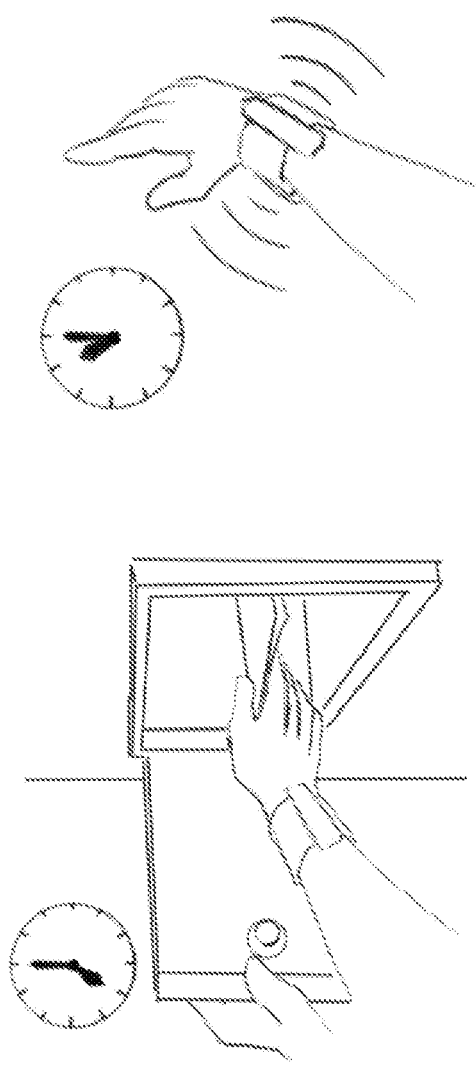
FIG. 3B is an illustration demonstrating one application of the device of the present disclosure for returning items to a safe or other container.
Figure 3C:
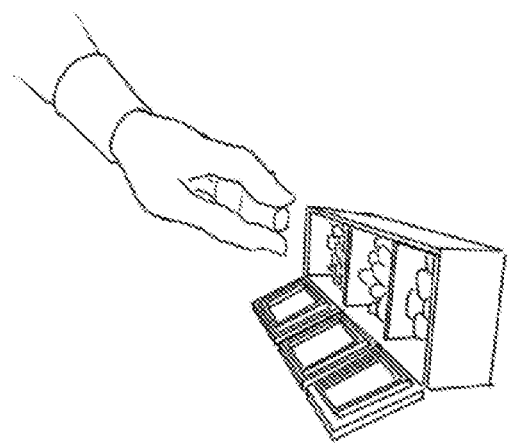
FIG. 3C is an illustration demonstrating one application of the device of the present disclosure where a user has forgotten to take pills and it is useful to revisit activity monitoring by way of the subject device to determine if the pills have been consumed.
Figure 3C:

Referring to block 1010 of process 1000 and to the Object Spatial Contextual Recall of FIG. 2H, the device 102 of the system may be further leveraged to identify a present location of an object of interest, or the pill continuing the example of FIG. 3C. As indicated in FIG. 3C, the pill is ultimately consumed, but the system 100 is operable to at least identify a last known location of the pill. Such object detection and recall is particularly advantageous for locating a lost item, such as a wallet or credit card (FIG. 3A). As indicated in FIG. 3A, an alert can prompt a user wearing the device 102 as to the present location of an object of interest.

To illustrate such present location detection in view of the pill example of FIG. 3C, a Spatial Contextual Engine (SCE) 432 implemented by one or more of the processing modules 400 retrieves one or more of the Inflection Points 313 of the last Grasping-Release Cycle for the pill, identified in blocks 1006 and 1008. The Inflection Point corresponding to the release of the pill is then used to locate from the video store 301 the video frames captured by the dorsal camera 155 just before and after the pill has been released. The retrieved video is sent to the touch sensitive display 201 of the mobile device 103, where the user can then scroll through the video in both directions, freeze on a frame at any time, and zoom in and out; all under finger control, or via haptics. In the instant case, the user can view the final images of the pill being released into his/her own mouth, confirming that the user has consumed the pill and that the present location of the pill is within the body of the user.

Stated another way, once the SCE 432 implemented by one or more of the processing modules 400 retrieves one or more of the Inflection Points 313 of the last Grasping-Release Cycle for the pill, a set of image frames is identified from the camera data of the second multimodal dataset; the set of image frames being captured during a portion of the time period as the object of interest is released. As such, the set of image frames are extracted from portions of the time period (T) where inflection points are identified corresponding to a release of the object. In addition, a subset of the set of image frames may be identified by the by one or more of the processing modules 400; the subset defining a release hand movement by the user of the object of interest. These images may be provided to the user via the mobile device 103 or in any form, to confirm the present location of the pill.

It should be appreciated that in some embodiments, the device 102 of the system can be implemented to identify inflection points or other activity of the hands without an object of interest, while still leveraging various novel feature described herein. For example, the training methods and features described herein can be implemented to train, tune, and implement any number of machine learning models to detect inflection points associated with seizure activity in view of the multimodal data generated by the device. In this manner, for example, the system 100 can be leveraged to identify when the user is suffering from a seizure, by identifying particular inflection points of the hand associated with muscle spasm activity and abnormal positioning of the fingers and hands relative to the wrist, or other activity indicative of a seizure. Localization aspects and other features of the multimodal data can further indicate if the hand of the user has moved to a floor, indicating that the user has collapsed during the seizure, for example.

Exemplary Computing Device

Figure 5:
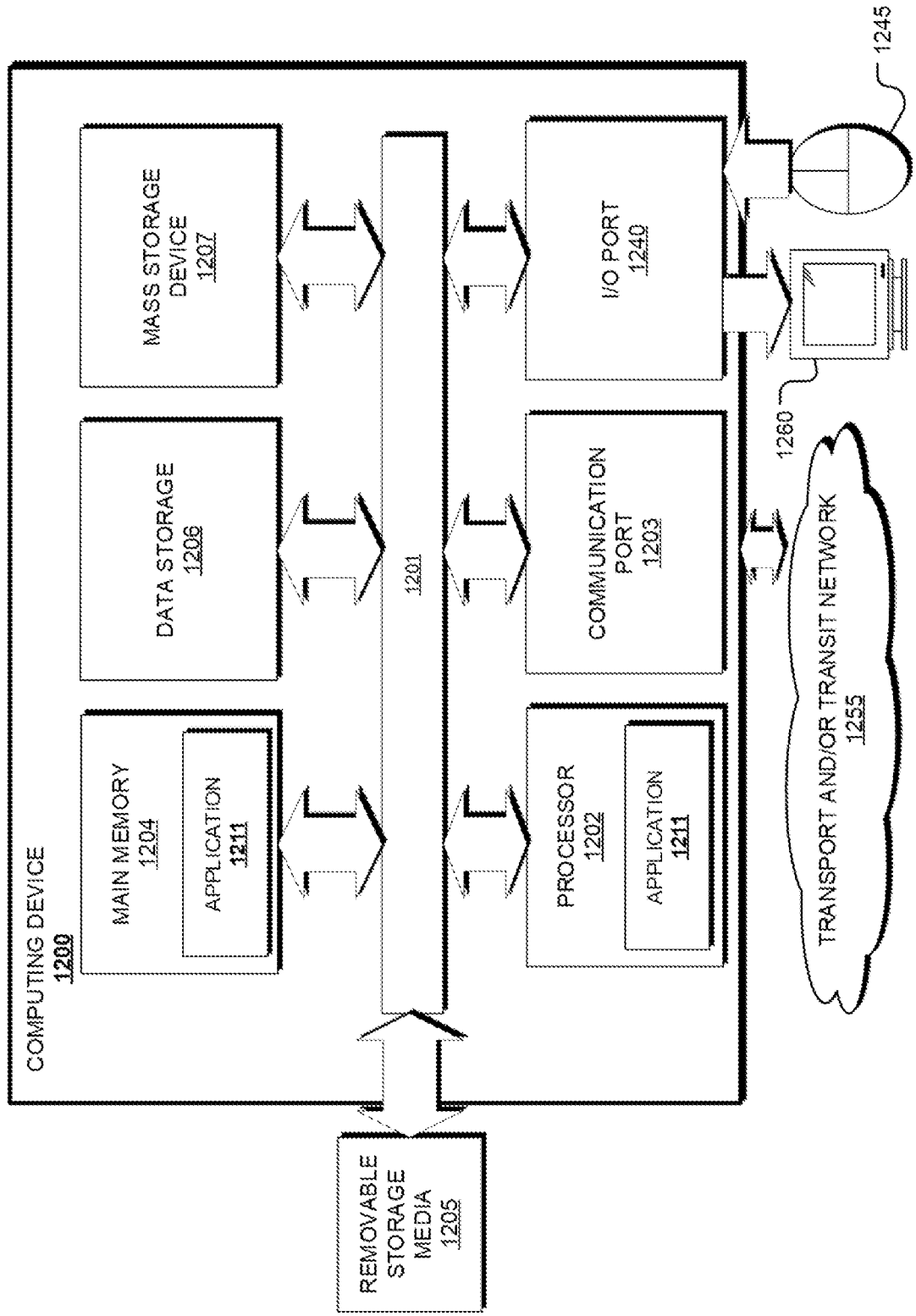
FIG. 5 is a simplified block diagram of an exemplary computing device that may be implemented along with the device described herein to execute functionality described herein.

Referring to FIG. 5, a computing device 1200 is illustrated which may take the place of the computing device 102 and be configured, via one or more of an application 1211 or computer-executable instructions, to execute personalized activity tracking functionality described herein. More particularly, in some embodiments, aspects of the methods herein may be translated to software or machine-level code, which may be installed to and/or executed by the computing device 1200 such that the computing device 1200 is configured for personalized activity tracking, and other functionality described herein. It is contemplated that the computing device 1200 may include any number of devices, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments, and the like.

The computing device 1200 may include various hardware components, such as a processor 1202, a main memory 1204 (e.g., a system memory), and a system bus 1201 that couples various components of the computing device 1200 to the processor 1202. The system bus 1201 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computing device 1200 may further include a variety of memory devices and computer-readable media 1207 that includes removable/non-removable media and volatile/nonvolatile media and/or tangible media, but excludes transitory propagated signals. Computer-readable media 1207 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computing device 1200. Communication media includes computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The main memory 1204 includes computer storage media in the form of volatile/nonvolatile memory such as read only memory (ROM) and random access memory (RAM). A basic input/output system (BIOS), containing the basic routines that help to transfer information between elements within the computing device 1200 (e.g., during start-up) is typically stored in ROM. RAM typically contains data and/or program modules that are immediately accessible to and/or presently being operated on by processor 1202. Further, data storage 1206 in the form of Read-Only Memory (ROM) or otherwise may store an operating system, application programs, and other program modules and program data.

The data storage 1206 may also include other removable/non-removable, volatile/nonvolatile computer storage media. For example, the data storage 1206 may be: a hard disk drive that reads from or writes to non-removable, nonvolatile magnetic media; a magnetic disk drive that reads from or writes to a removable, nonvolatile magnetic disk; a solid state drive; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media provide storage of computer-readable instructions, data structures, program modules, and other data for the computing device 1200.

A user may enter commands and information through a user interface 1240 (displayed via a monitor 1260) by engaging input devices 1245 such as a tablet, electronic digitizer, a microphone, keyboard, and/or pointing device, commonly referred to as mouse, trackball or touch pad. Other input devices 1245 may include a joystick, game pad, satellite dish, scanner, or the like. Additionally, voice inputs, gesture inputs (e.g., via hands or fingers), or other natural user input methods may also be used with the appropriate input devices, such as a microphone, camera, tablet, touch pad, glove, or other sensor. These and other input devices 1245 are in operative connection to the processor 1202 and may be coupled to the system bus 1201, but may be connected by other interface and bus structures, such as a parallel port, game port or a universal serial bus (USB). The monitor 1260 or other type of display device may also be connected to the system bus 1201. The monitor 1260 may also be integrated with a touch-screen panel or the like.

The computing device 1200 may be implemented in a networked or cloud-computing environment using logical connections of a network interface 1203 to one or more remote devices, such as a remote computer. The remote computer may be a personal computer, a server, a router, a network PC, a peer device or other common network node, and typically includes many or all of the elements described above relative to the computing device 1200. The logical connection may include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computing device 1200 may be connected to a public and/or private network through the network interface 1203. In such embodiments, a modem or other means for establishing communications over the network is connected to the system bus 1201 via the network interface 1203 or other appropriate mechanism. A wireless networking component including an interface and antenna may be coupled through a suitable device such as an access point or peer computer to a network. In a networked environment, program modules depicted relative to the computing device 1200, or portions thereof, may be stored in the remote memory storage device.

Certain embodiments are described herein as including one or more modules. Such modules are hardware-implemented, and thus include at least one tangible unit capable of performing certain operations and may be configured or arranged in a certain manner. For example, a hardware-implemented module may comprise dedicated circuitry that is permanently configured (e.g., as a special-purpose processor, such as a field-programmable gate array (FPGA) or an application-specific integrated circuit (ASIC)) to perform certain operations. A hardware-implemented module may also comprise programmable circuitry (e.g., as encompassed within a general-purpose processor or other programmable processor) that is temporarily configured by software or firmware to perform certain operations. In some example embodiments, one or more computer systems (e.g., a standalone system, a client and/or server computer system, or a peer-to-peer computer system) or one or more processors may be configured by software (e.g., an application or application portion) as a hardware-implemented module that operates to perform certain operations as described herein.

Accordingly, the term "hardware-implemented module" encompasses a tangible entity, be that an entity that is physically constructed, permanently configured (e.g., hardwired), or temporarily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure the processor 1202, for example, to constitute a particular hardware-implemented module at one instance of time and to constitute a different hardware-implemented module at a different instance of time.

Hardware-implemented modules may provide information to, and/or receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and may store the output of that operation in a memory device to which it is communicatively coupled. A further hardware-implemented module may then, at a later time, access the memory device to retrieve and process the stored output. Hardware-implemented modules may also initiate communications with input or output devices.

Computing systems or devices referenced herein may include desktop computers, laptops, tablets e-readers, personal digital assistants, smartphones, gaming devices, servers, and the like. The computing devices may access computer-readable media that include computer-readable storage media and data transmission media. In some embodiments, the computer-readable storage media are tangible storage devices that do not include a transitory propagating signal. Examples include memory such as primary memory, cache memory, and secondary memory (e.g., DVD) and other storage devices. The computer-readable storage media may have instructions recorded on them or may be encoded with computer-executable instructions or logic that implements aspects of the functionality described herein. The data transmission media may be used for transmitting data via transitory, propagating signals or carrier waves (e.g., electromagnetism) via a wired or wireless connection.

It should be understood from the foregoing that, while particular embodiments have been illustrated and described, various modifications can be made thereto without departing from the spirit and scope of the inventive concept described herein as will be apparent to those skilled in the art. Such changes and modifications are within the scope and teachings of this concept as defined in the claims appended hereto.

What is claimed is:

1. A system for personalized activity monitoring, comprising:
   a device that provides a wrist-centric view of activity of a hand to identify a predetermined task performed by the hand relative to an object of interest, the device including a plurality of cameras, a plurality of sensors, and a microcontroller in operable communication with the plurality of sensors and the plurality of cameras, wherein to identify the predetermined task, the microcontroller of the device:
      detects the object of interest from a multimodal dataset including video data generated by the plurality of cameras and localization data generated by the plurality of sensors; and
      extracts inflection points from the multimodal dataset by a filter that parses the multimodal dataset into a plurality of segments defining the inflection points, the inflection points corresponding to movement of the hand and fingers of the hand, at least one of the inflection points corresponding to the predetermined task associated with the object of interest such that the microcontroller confirms the predetermined task associated with the object of interest was performed;
      wherein the microcontroller identifies a present location of the object of interest by referencing video stream data from the plurality of cameras corresponding to time-stamps of the inflection points to track, frame-by-frame, a position of the object of interest relative to the device over time.

2. The system of claim 1, wherein the microcontroller executes an object specific neural network to detect the object of interest, the object specific neural network generated from a convolutional neural network trained to performed object detection with an annotated object training set generated from engagement of the device by a user, the object specific neural network operable to identify specific objects of interest associated with the user.

3. The system of claim 1, wherein the multimodal dataset defines object identification and tracking information, designated locations and locales information, and inflection points.

4. The system of claim 1, wherein the plurality of cameras of the device includes a dorsal camera positioned along the wrist of the hand to capture an immediate environment proximate to the hand, and a ventral camera positioned along a ventral side of the hand that captures images of the hand, fingers of the hand, and predetermined objects of interest.

5. The system of claim 1, wherein the plurality of sensors includes an inertial sensor that measures acceleration of the device.

6. The system of claim 1, wherein the plurality of sensors includes a pressure sensor that measures displacement indicative of activity of muscles and tendons of the hand.

7. The system of claim 1, wherein the plurality of segments are fed to a predetermined machine learning model that is pre-trained to identify classes associated with predetermined actions of the hand, different modalities of the multimodal dataset accommodating efficient identification and distinction between the predetermined actions of the hand.

8. The system of claim 1, wherein the object of interest is defined by a user during an initialization process such that the device is customized to an individual's requirements.

9. The system of claim 1, wherein the microcontroller tracks past movement of the device and the object of interest over time, and links activity of the object of interest to predefined locales and locations.

10. The system of claim 1, wherein the microcontroller operates under a semi-autonomous mode, such that the device detects frequently occurring patterns associated with a user of the device for identification and subsequent monitoring by the device.

11. A method for personalized activity tracking using hands of a user, comprising:
   configuring a device to identify an engagement of an object of interest by a user, comprising:
      training a first neural network, using one or more processing modules, to detect an object of interest by feeding the first neural network with a first multimodal dataset generated from the device, the first multimodal dataset generated by a plurality of sensors and a plurality of cameras that capture images of the object of interest and monitor a hand movement of the user while the user engages the object of interest with the hand, and
      training a second neural network, using the one or more processing modules, to identify and classify an inflection point associated with the hand movement from the first multimodal dataset; and
   detecting the object of interest and tracking the engagement of the object of interest from a second multimodal dataset generated by the device, by:
      detecting a hand movement associated with one or more inflection points corresponding to the object of interest over a time period,
      applying, by the one or more processing modules, the second multimodal dataset to the first neural network to identify the object of interest from camera data of the second multimodal dataset captured during the time period, and
      applying, by the one or more processing modules, the second multimodal dataset to the second neural network to identify the inflection point.

12. The method of claim 11, further comprising:
   generating, by the device, the first multimodal dataset as the user grasps, displaces, and releases the object of interest a predetermined number of times.

13. The method of claim 12, further comprising:
   generating, by the device, a plurality of first multimodal datasets as the user grasps, displaces, and releases each of a plurality of objects of interest a predetermined number of times; and
   generating, by the one or more processing modules, an annotated object training from the plurality of first multimodal datasets that maps a set of movements of the hand of the user to each of the plurality of objects of interest.

14. The method of claim 13, further comprising:
   generating an object specific neural network by feeding the annotated object training set to the first neural network, the object specific neural network trained to identify specific ones of the plurality of objects of interest.

15. The method of claim 11, further comprising:
identifying a present location of the object of interest by retrieving a set of image frames of the camera data captured during a portion of the time period as the object of interest is released; and
indicating a subset of the set of image frames defining a release hand movement by the user of the object of interest.

16. A device for personalized activity tracking using the hands, comprising: a plurality of cameras that capture camera data of wrist-centric views of activity of the hands of a user; a plurality of sensors; and a microcontroller in operable communication with the plurality of cameras and the plurality of sensors, the microcontroller adapted to extract inflection points from a multimodal dataset generated by the plurality of cameras and the plurality of sensors to identify a predetermined task performed with the hands of the user; wherein the inflection points correspond to unique movements of the hand that the user performs to complete the predetermined task and engage an object of interest.

17. The device of claim 16, wherein the plurality of cameras of the device includes a dorsal camera positioned along the wrist of the hand to capture an immediate environment proximate to the hand, and a ventral camera positioned along a ventral side of the hand that captures images of the hand, and fingers of the hand.

* * * * *